United States Patent [19]
Cliffe et al.

[11] Patent Number: 5,610,295
[45] Date of Patent: Mar. 11, 1997

[54] 4-AMINO-2-(HETERO)ARYL-BUTANAMIDES USEFUL AS 5-HT$_{1A}$-ANTAGONISTS

[75] Inventors: Ian A. Cliffe, Slough; Anderson D. Ifill, Oxford, both of England

[73] Assignee: John Wyeth & Brother, Ltd., England

[21] Appl. No.: 436,410

[22] PCT Filed: Feb. 25, 1994

[86] PCT No.: PCT/GB94/00372

§ 371 Date: May 24, 1995

§ 102(e) Date: May 24, 1995

[87] PCT Pub. No.: WO94/20481

PCT Pub. Date: Sep. 15, 1994

[30] Foreign Application Priority Data

Mar. 6, 1993 [GB] United Kingdom ............... 9304632

[51] Int. Cl.$^6$ .................. C07D 405/06; A61K 31/55
[52] U.S. Cl. .................. 540/596; 540/597; 540/599; 540/602; 540/607
[58] Field of Search ............... 540/596, 597, 540/599, 602, 607; 514/212

[56] References Cited

FOREIGN PATENT DOCUMENTS

| | | |
|---|---|---|
| 0395244 | 4/1990 | European Pat. Off. . |
| 0452204 | 4/1991 | European Pat. Off. . |
| 0478954 | 8/1991 | European Pat. Off. . |
| 0481744 | 10/1991 | European Pat. Off. . |

*Primary Examiner*—Joseph McKane
*Assistant Examiner*—Richard S. Myers, Jr.
*Attorney, Agent, or Firm*—R. F. Boswell, Jr.

[57] ABSTRACT

Amide Derivatives of formula (I): $R^5NR^4(CR_2)_2CHR^3CONR^1R^2$ and their pharmaceutically acceptable salts are 5-HT1A binding agents and may be used, for example, as anxiolytics. The radicals, R, $R^1$, $R^2$, $R^3$, $R^4$ and $R^5$ have specified meanings.

16 Claims, No Drawings

4-AMINO-2-(HETERO)ARYL-BUTANAMIDES USEFUL AS 5-HT$_{1A}$-ANTAGONISTS

This application is a National Stage filing under 35 U.S.C. § 372 of PCT/GB94/00372, filed Feb. 25, 1994.

This invention relates to novel amide derivatives, to processes for their preparations, to their use and to pharmaceutical compositions containing them. The novel compounds act on the central nervous system by binding to 5-HT receptors (as more fully explained below) and hence can be used as medicaments for treating humans and other mammals.

EP-A-0481744 discloses that 2,3,4,5,6,7-hexahydro 1-{4-[1-[4-(2-methoxyphenyl)piperazinyl]]-2-phenylbutyryl}-1H-azepine and its salts are 5-HT$_{1A}$ binding agents useful, for example as anxiolytics.

The novel compounds of the invention are those of general formula (I)

$$R^5NR^4(CR_2)_2CHR^3CONR^1R^2 \qquad (I)$$

and the pharmaceutically acceptable salts thereof.

In formula (I)
each R is independently hydrogen or lower alkyl,
$R^1$ is hydrogen or lower alkyl,
$R^2$ is lower alkyl, cycloalkyl, cycloalkyl(lower)alkyl or aryl(lower)alkyl,
or $R^1$ and $R^2$ together with the nitrogen atom to which they are both attached represent an azetidino, pyrrolidino, piperidino, hexahydroazepino, morpholino or piperazino ring which may be optionally substituted by one or more lower alkyl, aryl or aryl(lower)alkyl groups,
$R^3$ is an aryl or heteroaryl radical,
$R^4$ is hydrogen or lower alkyl,
and $R^5$ is a group of formula

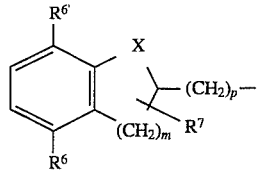 (A)

where X is —(CH$_2$)$_n$—, —OCH$_2$— or —SCH$_2$—, m is 0 or 1, n is 1, 2 or 3 and p is 0 or 1 such that (m+p) is 1 and that (m+n) is 1, 2 or 3,
$R^6$ is hydrogen, lower alkyl, lower alkoxy, hydroxy, halogen, trifluoromethyl, (lower)alkoxycarbonyl, carboxamido, nitro, cyano, amino, (lower)alkylamino, di(lower)alkylamino or (lower) alkylcarbonyl,
$R^{6'}$ is hydrogen or halogen when X is —(CH$_2$)$_n$— and $R^{6'}$ is hydrogen when X is —OCH$_2$— or —SCH$_2$—,
$R^7$ is hydrogen or lower alkyl or

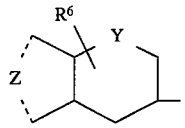 (B)

where Y is —O—, —S— or —CH$_2$—,
Z represents a heteroaromatic ring fused on to the non-aromatic ring containing the Y group
and $R^6$ is as defined above and one or more $R^6$ groups may be attached to the heteroaromatic ring and/or the non-aromatic ring or $$R^8\text{—}CH_2CH_2\text{—} \qquad (C)$$

where $R^8$ is a monocyclic or bicyclic heteroaryl group or

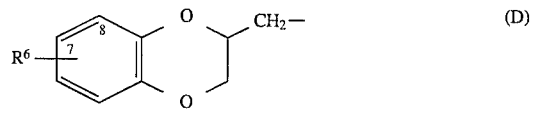 (D)

where $R^6$ is as defined above and the indicated 7, 8 positions may optionally be fused with a heteroaromatic ring or a further aromatic ring or $$R^9OCH_2CHOHCH_2\text{—} \qquad (E)$$

where $R^9$ is a mono or bicyclic aryl or bicyclic heteroaryl group or $$R^9OCH_2CH_2\text{—} \qquad (F)$$

where $R^9$ is as defined above.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, isobutyl, tert-butyl, pentyl and isopentyl.

Examples of cycloalkyl groups are groups containing 3 to 8 carbon atoms e.g. cyclopentyl, cyclohexyl and cycloheptyl.

When used herein "aryl" means an aromatic radical having 6 to 12 carbon atoms (e.g. phenyl or naphthyl) which optionally may be substituted by one or more substituents. Preferred substituents are lower alkyl, lower alkoxy (e.g. methoxy, ethoxy, propoxy, butoxy), halogen (e.g. chlorine), halo(lower)alkyl (e.g. trifluoromethyl), nitro, nitrile, amido, (lower)alkoxycarbonyl, amino, (lower)alkylamino and di(lower)alkylamino.

The term "heteroaryl" refers to an aromatic radical containing one or more (e.g. 1, 2 or 3) hetero ring atoms (e.g. oxygen, nitrogen, sulphur) and which may be optionally substituted by one or more substituents. Examples of suitable substituents are given above in connection with "aryl" radicals. The heteroaryl radical may, for example, contain 5 to 10 ring atoms. Unless specified otherwise the heteroaryl radical is preferably mono- or bicyclic. A monocyclic radical may, for example, contain 5 to 7 ring atoms. Preferably the hetero ring contains a nitrogen atom with or without one or more further hetero atoms. Examples of heteroaryl groups include, for example, pyrimidinyl, pyrazinyl, quinolinyl, isoquinolinyl and indolyl each of which may be optionally substituted as mentioned above.

When a "heteroaromatic ring" is fused on to a non-aromatic ring (as in formula B) or is fused on to an aromatic ring (as in formula D) the "heteroaromatic ring" may be a fused "heteroaryl" group where heteroaryl is defined above.

Examples of the preferred meanings of the various substituents in formula (I) are given below:

Both R groups are hydrogen,
$R^1$ is hydrogen and $R^2$ is cycloalkyl, in particular cyclohexyl or cycloheptyl or more preferably $R^1$ and $R^2$ together with the nitrogen atom to which they are both attached represent

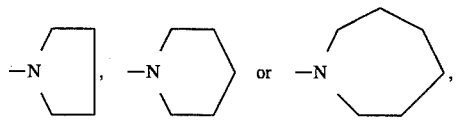

$R^3$ is preferably an optionally substituted phenyl group,
$R^4$ is preferably hydrogen, methyl or propyl, A is preferably a group of formula:

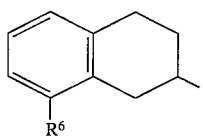

where $R^6$ is as defined above, particularly lower alkoxy,
B is preferably a group of formula:

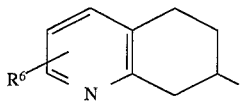

where $R^6$ is as defined above,
C is preferably a group of formula

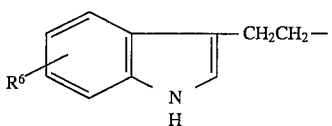

where $R^6$ is as deemed above, particularly lower alkoxy,
D is preferably a group of formula

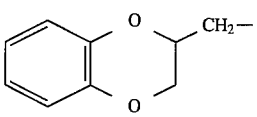

E is preferably a group of formula

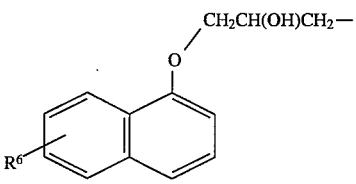

where $R^6$ is as defined above,
F is preferably a group of formula

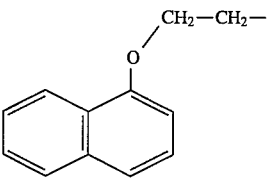

The compounds of the invention may be prepared by methods known in the art from known starting materials or starting materials that may be prepared by conventional methods.

In one method of preparing the compounds of the invention an amine of formula $$NHR^1R^2 \qquad (II)$$

(where $R^1$ and $R^2$ are as defined above) is acylated with an acid of formula $$R^5NR^4(CR_2)_2CHR^3COOH \qquad (III)$$

(where R, $R^3$, $R^4$ and $R^5$ are as defined above) or with an acylating derivative thereof. Examples of acylating derivatives include the acid halides (e.g. chlorides), azides, anhydrides, imidazolides (e.g. obtained from carbonyldiimidazole), activated esters or O-acyl ureas obtained from a carbodiimide such as a dialkylcarbodiimide, particularly dicyclohexylcarbodiimide. Preferably the amine is acylated with the acid in presence of a coupling agent such as 1,1'-carbonyldiimidazole, iso-butylchloroformate or diphenylphosphinyl chloride.

An alternative method of preparing the compounds of formula (I) comprises alkylating an amine of formula $$R^5NHR^4 \qquad (IV)$$

with an alkylating agent providing the group $$-(CR_2)_2CHR^3CONR^1R^2 \qquad (V)$$

(where R, $R^1$, $R^2$ and $R^3$ are as defined above). The alkylating agent may be, for example, a compound of formula $$Q-(CR_2)_2CHR^3CONR^1R^2 \qquad (VI)$$

where R, $R^1$, $R^2$ and $R^3$ are as defined above and Q is a leaving group such as halogen or an alkyl- or aryl-sulphonyloxy group.

Another method of preparing the compounds of the invention comprises reacting a compound of formula $$R^5NR^4(CR_2)_2.Q^1 \qquad (VII)$$

(where R, $R^4$ and $R^5$ are as defined above and $Q^1$ is a leaving group, e.g. halogen) with an anion of the amide of formula $$R^3CH_2CONR^1R^2 \qquad (VIII)$$

(where $R^1$, $R^2$ and $R^3$ are as defined above). The anion may be prepared by reacting the amide with a strong base, e.g. potassium hydride.

A further method of preparing the compounds of the invention involves reacting an amine of formula (IV)

$$R^5NHR^4 \qquad (IV)$$

with an aldehyde of formula $$OHC(CR^2)CHR^3CONR^1R^2 \qquad (IX)$$

either in the presence of a reducing agent such as sodium cyanoborohydride or sodium triacetoxyborohydride or followed by reduction, eg using catalytic hydrogenation, to give a corresponding compound of formula I. The aldehyde of formula (IX) can be prepared from an alcohol of formula $$HO(CR_2)CHR^3CONR^1R^2 \qquad (X)$$

by oxidation with, for example, a chromium (VI) reagent such as pyridinium dichromate or a Swern reagent such as dimethyl sulphoxide/oxalyl chloride.

Yet a further method of preparing compounds of formula I as defined above comprises reacting an amine of formula $$HNR^4(CR_2)_2CHR^3CONR^1R^2 \qquad (XI)$$

wherein R, $R^1$, $R^2$, $R^3$ and $R^4$ are as defined above with a compound of formula:

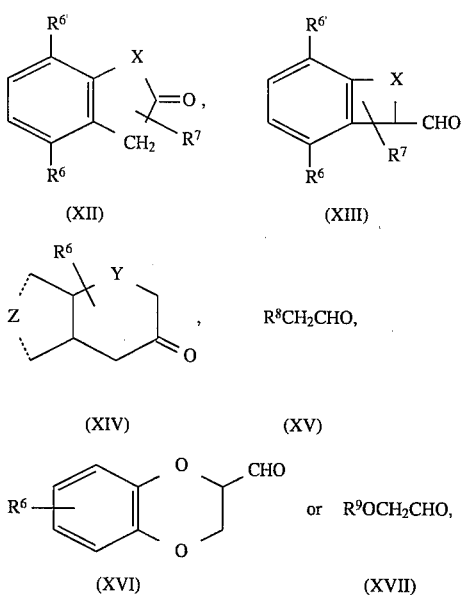

wherein $R^6$, $R^{6'}$, $R^7$, $R^8$, $R^9$, X, Y and Z are as defined above and n is 1, 2 or 3, followed by reduction or catalytic hydrogenation to give a corresponding compound of formula I.

If in any of the other processes mentioned herein, a substituent on the group $R^3$ or $R^5$ is other than the one required the substituent may be converted to the desired substituent by known methods. A substituent on $R^3$ or $R^5$ may also need protecting against the conditions under which the reaction is carried out. In such a case the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different stereoisomeric forms. The compounds can be for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. The compounds particularly bind to receptors of the 5-HT$_{1A}$ type. The compounds of the invention can be used for the treatment of CNS disorders, such as anxiety in mammals, particularly humans. They may also be used as antidepressants, antipsychotics, hypotensives and as agents for regulating the sleep/wake cycle, feeding behaviour and/or sexual function and for treating cognition disorders.

The compounds of the invention are tested for 5-HT$_{1A}$ receptor binding activity in rat hippocampal membrane homogenate by the method of B S Alexander and M D Wood, J Pharm Pharmacol, 1988, 40, 888–891.

The compounds are tested for 5-HT$_{1A}$ receptor antagonism activity in a test involving the antagonism of 5-carboxamidotryptamine in the guinea-pig ileum in vitro (based upon the procedure of Fozard et at, Br J Pharmac, 1985, 86, 601P).

The invention also provides a pharmaceutical composition comprising a compound of formula I or a pharmaceutically acceptable acid addition salt thereof in association with a pharmaceutically acceptable carrier. Any suitable carrier known in the an can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the Shape and size desired. The powders and tablets preferably contain up to 99%, e.g. from 0.03 to 99% preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution, alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compostions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

N-(2-(1,2,3,4,-Tetrahydro-8-methoxynaphthyl))-N-methyl-1-(4-amino-2-phenylbutanoyl)-2,3,4,5,6,7-hexahydro-1H-azepine A stirred solution of N-methyl-2-(1,2,3,4-tetrahydro-8-methoxy)naphthylamine (0.1 mol), di-isopropylethylamine (0.1 mol), and potassium iodide (0.1 mol) in dimethylformamide (200 ml) is treated under an atmosphere of argon with 2,3,4,5,6,7-hexahydro-1-(4-chloro-2-phenylbutanoyl)-1H-azepine (0.1 mol) in DMF (50 ml), heated at 100° C. for 3 hours, cooled to room temperature, and poured into water (250 ml). The mixture is extracted with ethyl acetate (2×250 ml) and the extracts washed with water (2×250 ml), dried (MgSO$_4$), and evaporated in vacuo. The residue is purified by column chromatography (silica; ethyl acetate) to give the product.

EXAMPLE 2

N-(7-(5,6,7,8-Tetrahydroquinolinyl))-N-methyl-1-(4-amino-2-phenylbutanoyl)-2,3,4,5,6,7-hexahydro-1H-azepine This compound is prepared following the procedure of Example 1 but using N-methyl-5,6,7,8-hexahydroquinolinyl-7-amine (0.1 mol) in place of N-methyl-2-(1,2,3,4-tetrahydro-8-methoxy)naphthylamine.

EXAMPLE 3

N-(2-(3-(5-Methoxyindolyl))ethyl)-N-methyl-1-(4-amino-2-phenylbutanoyl)-2,3,4,5,6,7-hexahydro-1H-azepine This compound is prepared following the procedure of Example 1 but using 5-methoxy-N-methyltryptamine (0.1 mol) in place of N-methyl-2-(1,2,3,4-tetrahydro-8-methoxy)naphthylamine.

EXAMPLE 4

1-(4-(2-(2,3-Dihydro-1,4-benzodioxinyl)methylamino)-2-phenylbutanoyl)-2,3,4,5,6,7-hexahydro-1H-azepine This compound is prepared following the procedure of Example 1 but using 2,3-dihydro-1,4-benzodioxin-2-ylmethylamine (0.1 mol) in place of N-methyl-2-(1,2,3,4-tetrahydro-8-methoxy)naphthylamine.

EXAMPLE 5

1-(4-(1-(2-Hydroxy-3-(1-naphthyloxy)propyl)amino)-2-phenylbutanoyl)-2,3,4,5,6,7-hexahydro-1H-azepine This compound is prepared following the procedure of Example 1 but using 2-hydroxy-3-(1-naphthyloxy)propanolamine (0.1 mol) in place of N-methyl-2-(1,2,3,4-tetrahydro-8-methoxy)naphthylamine.

EXAMPLE 6

1-(4-(N-(2-(1-Naphthyloxy)ethyl)-N-propylamino)-2-phenylbutanoyl)-2,3,4,5,6,7-hexahydro-1H-azepine This compound is prepared following the procedure of Example 1 but using N-(2-(1-naphthyloxy)ethyl)-N-propylamine in place of N-methyl-2-(1,2,3,4-tetrahydro-8-methoxy)naphthylamine.

EXAMPLE 7

N-(2-(1,2,3,4-Tetrahydro-8-methoxynaphthyl))-1-(4-amino-2-phenylbutanoyl)-2,3,4,5,6,7-hexahydro-1H-azepine (a)  2,3,4,5,6,7-Hexahydro-1-(4-chloro-2-phenylbutanoyl)-1H-azepine A solution of thionyl chloride (12.24 g, 0.103 mol) in dichloromethane (50 ml) was added dropwise to a solution of 4-bromo-2-phenylbutanoic acid (25.08, 0.103 mol) in dichloromethane (200 ml). A few drops of N,N-dimethylformamide were added and the reaction mixture stirred overnight. A few more drops of N,N-dimethylformamide were added and, after stirring for 1 h, a solution of hexamethyleneimine (11.22 g, 0.113 mol) in dichloromethane (120 ml) was added followed by a solution of diisopropylethylamine in dichloromethane (50 ml). The reaction mixture was stirred overnight, washed with brine (100 ml), sodium hydroxide (2M, 100 ml) and brine (100 ml), dried (MgSO$_4$), and concentrated under reduced pressure to afford an oil (20.04 g) which solidified on standing. The solid was recrystallised from hexane to give the product as colourless crystals (12.86 g), m.p. 50°–53° C.

(b) N-(2-(1,2,3,4-Tetrahydro-8-methoxynaphthyl))-1-(4-amino-2-phenylbutanoyl)-2,3,4,5,6,7-hexahydro-1H-azepine A mixture of 2-amino-8-methoxytetralin hydrochloride (1.67 g, 7.81 mmol), the product of step (a) (2.19 g, 7.83 mmol), diisopropylethylamine (2.02 g, 15.6 mmol) and sodium iodide (1.17 g, 7.81 mmol) in N,N-dimethylformamide (25 ml) was heated at 80° C. for 3 h and then left stirring overnight at room temperature. The reaction mixture was poured into water (130 ml) and the aqueous media washed with ethyl acetate (3×50 ml). The combined organic phases were washed with brine (50 ml), water (50 ml), dried (sodium sulphate) and concentrated to afford a brown oil (3.20 g). The oil was chromatographed on alumina (1CN Alumina, Act 11–111 ), gradient eluting with ethyl acetate-:hexane (1:2 to 1:1) to afford the title compound as an oil as a 1:1 mixture of two diastereomors (0.59 g). Found: C, 75.1; H, 8.6; N, 6.5. $C_{27}H_{36}N_2O_2.\tfrac{2}{3}H_2O$ requires: C, 75.0; H, 8.7; N. 6.5%. $^1$H NMR $\delta_H$ (400 MHz; CDCl$_3$) 1.2–1.8 (8H, m) and 3.3–3.6 (4H, m) (hexahydroazepine); 1.7 (1H, m), 2.1 (1H, m), 2.4 (1H, m) and 2.8–3.1 (4H, m) (tetrahydronaphthalene); 2.0 (1H, m), 2.3 (1H, m), 2.7 (2H, m) and 4.02 (1H, m) (CH$_2$CH$_2$CHCO); 3.798 and 3.802 (3H, 2 x s, OMe);6.64

(1H, d), 6.70 (1H, d) and 7.08 (1H, t) (tetrahydronaphthalene); and 7.2–7.4 (5H, m, Ph).

EXAMPLE 8

N-(7-(5,6,7,8-Tetrahydroquinolinyl))-N-methyl-1-(4-amino-2-phenylbutanoyl)-2,3,4,5,6,7-hexahydro-1H-azepine (a) 2,3,4,5,6,7-Hexahydro-1-(4-hydroxy-2-phenylbutanoyl)-1H-azepine 2,3,4,5,6,7-Hexahydro-1H-azepine (3.36 g, 33.9 mmol) in 1,2-dichloroethane (10 ml) was added to a cooled (ice/water) solution of triethylamine (4.68 g, 46.2 mmol) and aluminium trichloride (4.52 g, 33.9 mmol) in 1,2-dichloroethane (70 ml). A solution of 2-phenylbutyrolactone (5.00 g, 30.8 mmol) in 1,2-dichloroethane (50 ml) was added to the cooled reaction mixture and stirring continued overnight. The reaction mixture was poured into water (150 ml), basified with 2M-NaOH, and washed with ethyl acetate (3×80 ml). The combined organic phases were washed with brine (80 ml) and water (80 ml), dried (MgSO$_4$), and concentrated in vacuo to afford a brown oil which partially solidified on standing. The crude product was chromatographed on silica gel, eluting with ethyl acetate to give the title compound as an oil (2.68 g, 33.3%).

(b) 2,3,4,5,6,7-Hexahydro-1-(3-formyl-2-phenylpropanoyl)-1H-azepine

Dimethylsulphoxide (3.97 g, 50.9 mmol) in dichloromethane (25 ml) was added to a solution of oxalyl chloride (3.09 g, 24.4 mmol) at −50° C. in dichloromethane (25 ml). The reaction mixture was kept at this temperature for 5 min, treated with a solution of the product of step (a) (5.54 g, 21.2 mmol) in dichloromethane (30 ml), and, after 1 h, treated with triethylamine (10.72 g, 0.106 mol). The cooling bath was removed and the reaction mixture allowed to warm to room temperature. Water (100 ml) was added and the separated aqueous phase washed with dichloromethane (50 ml). The combined organic phases were washed with brine (50 ml), water (50 ml), dried (Na$_2$SO$_4$) and concentrated in vacuo to afford the title compound as an oil (5.30 g, 96.4%).

(c) N-(7-(5,6,7,8-Tetrahydroquinolinyl))-N-methyl-1-(4-amino-2-phenylbutanoyl)-2,3,4,5,6,7-hexahydro-1H-azepine 7-(N-Methylamino)-5,6,7,8-tetrahydroquinoline, (1.53 g, 9.43 mmol), the product of step (b) (2.45 g, 9.43 mmol), sodium triacetoxyborohydride (2.20 g, 10.4 mmol) and acetic acid (0.62 g, 10.4 mmol) in 1,2-dichloroethane (20 ml) was stirred overnight at room temperature and diluted with water (40 ml). The separated aqueous phase was washed with dichloromethane (2×30 ml) and the combined organic phases washed with brine (40 ml), water (40 ml), dried (Na$_2$SO$_4$) and concentrated to afford an oil (8.57 g). The crude product was chromatographed on alumina, gradient eluting with hexane:ethyl acetate (3:1 to 1:2) to give an oil (1.65 g). The oil was dissolved in diisopropylether and acidified with ethereal hydrogen chloride to afford a pale orange powder which was recrystallised from ethyl acetate to give the title compound as the hydrochloride (0.57 g). $^1$H NMR $\delta_H$ (400 MHz; CD$_3$OD) 1.1–1.8 (8H, m) and 3.0–3.7 (4H, m) (hexahydroazepine); 2.0 (1H, m), 2.4 (1H, m), 3.0–3.7 (4H, m) and 4.0 (1H, m) (tetrahydroquinoline); 2.2 (1H, m), 2.5 (1H, m), 3.0–3.7 (2H, m) and 4.23 (1H, m) (CH$_2$CH$_2$CHCO); 2.96 (3H, br.s, NMe); 7.2–7.4 (5H, m, Ph); 7.85 (1H, 2 x dd, pyridine H3); 8.35 (1H, d, pyridine H4); and 8.66 (1H, 2 x d, pyridine H2).

EXAMPLE 9

1-(4-(2-(2,3-Dihydro-1,4-benzodioxinyl)methylamino)-2-phenylbutanoyl)-2,3,4,5,6,7-hexahydro-1H-azepine A solution of 2,3-dihydro-1,4-benzodioxin-2-ylmethylamine (2.00 g, 12.1 mmol) 2,3,4,5,6,7-hexahydro-1-[3-formyl-2-phenylpropanoyl]-1H-azepine (3.45 g, 13.3 mmol) and a catalytic amount of p-toluenesulphonic acid monohydrate in benzene (50 ml) was heated under reflux for 4 h. The reaction mixture was concentrated, redissolved in ethanol (20 ml) and added to a slurry of platinum oxide (0.36 g) in isopropanol (5 ml). The reaction mixture was hydrogenated in a Parr bottle at 50 psi overnight, filtered, and concentrated to afford the title compound as an oil (3.77 g, 76.2%).

EXAMPLE 10

N-(2-(1,2,3,4,-Tetrahydro-8-methoxynaphthyl))-N-methyl-1-(4-amino-2-phenylbutanoyl)-2,3,4,5,6,7-hexahydro-1H-azepine (a) 2,3,4,5,6,7-Hexahydro-1-[4-(N-benzyl-N-methylamino)-2-phenylbutanoyl]-1H-azepine A solution of 2,3,4,5,6,7-hexahydro-1-[4-chloro-2-phenylbutanoyl]-1H-azepine (10.0 g, 35.7 mmol) in acetonitrile (100 ml) was added to a solution of N-methylbenzylamine (4.03 g, 33.3 mmol) and diisopropylethylamine (4.62 g, 35.7 mmol) in acetonitrile (40 ml) and the reaction mixture stirred at room temperature overnight. The reaction mixture was concentrated under reduced pressure and the residue dissolved in water (100 ml). The aqueous phase was washed with ethyl acetate (3×50 ml) and the combined organic phases washed with brine (50 ml), water (50 ml), dried (MgSO$_4$) and concentrated under reduced pressure. The crude oil obtained was chromatographed on alumina, eluting with hexane:ethyl acetate (2:1) to afford the title compound as an oil (6.93 g, 53%).

(b) 2,3,4,5,6,7-Hexahydro-1-[4-(N-methylamino)-2-phenylbutanoyl]-1H-azepine

A solution of the product of step (a) (6.93 g, 19.0 mmol) in ethanol (60 ml) was added to a suspension of 10% Pd/C (10.67 g) in isopropanol (50 ml) plus 5 drops of concentrated hydrochloric acid. The reaction mixture was heated to 50° C. and 50 psi (about $3.5\times10^5$ Nm$^{-2}$) in a Parr bottle for 4 h. The catalyst was filtered off and the filtrate concentrated under reduced pressure to afford an oil. The oil was dissolved in water (80 ml), cooled (ice/water) and basified with aqueous sodium hydroxide (2M). The basic phase was washed with diethyl ether (3×50 ml) and the combined organic phases washed with brine (50 ml), water (50 ml), dried (MgSO$_4$) and concentrated to afford the title compound as an oil (3.38 g, 68%).

(c) N-(2-(1,2,3,4,-Tetrahydro-8-methoxynaphthyl))-N-methyl-1-(4-amino-2-phenylbutanoyl)-2,3,4,5,6,7-hexahydro-1H-azepine A solution of 8-methoxy-2-tetralone (10 mmol), the product of step (b) (10 mmol), and a catalytic amount of p-toluenesulphonic acid monohydrate in benzene (35 ml) is heated under reflux for 24 h. The reaction mixture is concentrated under reduced pressure, redissolved in ethanol (20 ml) and added to a suspension of platinum oxide (0.33 g) in isopropanol (10 ml). The reaction mixture is hydrogenated in a Parr bottle at 50 psi overnight. The reaction mixture is concentrated under reduced pressure and the crude product chromatographed on alumina, gradient eluting with ethyl acetate:hexane (3:1 to 1:1), to give the title product as an oil.

EXAMPLE 11

1-(4-(N-(5-Methoxy-3,4-dihydro-2H-1-benzopyran-3-yl)-N-methylamino)-2-phenylbutanoyl)-2,3,4,5,6,7-hexahydro-1H-azepine A solution of 5-methoxy-3,4-dihydro-2H-1-benzopyran-3-one (1.52 g, 8.53 mmol), 2,3,4,5,6,7-hexahydro-1-[4-(N-methylamino)-2-phenylbutanoyl]-1H-azepine (3.16 g, 11.5 mmol) and a catalytic amount of p-toluenesulphonic acid monohydrate in benzene (35 ml) was heated under reflux for 24 h. The reaction mixture was concentrated under reduced pressure, redissolved in ethanol (20 ml) and added to a suspension of platinum oxide (0.33 g) in isopropanol (10 ml). The reaction mixture was hydrogenated in a Parr bottle at 50 psi overnight. The reaction mixture was concentrated under reduced pressure and the crude product chromatographed on alumina, gradient eluting with ethyl acetate:hexane (3:1 to 1:1) to afford an oil (1.85 g, 49.7%). The oil was dissolved in diisopropylether (30 cm³), acidified with ethereal hydrogen chloride, and the pale yellow solid removed by filtration and dried in vacuo to give the monohydrochloride salt of the product as a mixture of four isomers (1.46 g), m.p. 95.1°–101.2° C. $^1$H NMR $\delta_H$ (400 MHz; CD$_3$OD) 1.1–1.7 (8H, m) and 3.0–3.7 (4H, m) (hexahydroazepine); 2.1 (1H, m), 2.4 (1H, m), 3.0–3.7 (2H, m) and 4.1 (1H, m) (CH$_2$CH$_2$CH); 2.92, 2.95 and 2.97 (3H, 3 x s, NMe); 3.0–3.7 (2H, m), 3.9 (1H, m), 4.2 (1H, m) and 4.4–4.6 (1H, m) (OCH$_2$CH$_2$H$_2$); 3.837, 3.844, 3.848 and 3.859 (3H, 4 x s, OMe); 6.52 (1H, m), 6.60 (1H, m) and 7.13 (1H, m) (benzopyran); and 7.2–7.4 (5H, m, Ph).

EXAMPLE 12

N-(2-(3-(5-Methoxyindolyl))ethyl)-N-methyl-1-(4-amino-2-phenylbutanoyl)-2,3,4,5,6,7-hexahydro-1H-azepine A solution of 5-methoxy-3-(2-(methylamino)ethyl)indole (0.6 g) and 1-(3-formyl-2-phenylpropanoyl)-2,3,4,5,6,7-hexahydroazepine (0.83 g) in dichloromethane (10 ml) containing acetic acid (0.2 ml) was treated with sodium triacetoxyborohydride (0.75 g). The reaction mixture was left to stir at 21° C. for 20 h and diluted with dichloromethane (100 ml) and water (100 ml). The aqueous phase was basified with solid sodium hydrogen carbonate and extracted into dichloromethane. The organic phases were combined, washed with brine, dried (MgSO$_4$), and evaporated under reduced pressure. The residue was purified by chromatography on silica using ethyl acetate as eluent to give the product (0.75 g). $^1$H NMR $\delta_H$ (200 MHz; CDCl$_3$) 1.2–1.8 (8H, m) and 3.2–3.7 (4H, m) (hexahydroazepine); 1.8 (1H, m), 2.3 (1H, m), 2.7 (2H, m) and 3.8 (1H, m) (CH$_2$CH$_2$CHCO); 2.35 (3H, s, NMe); 2.45 (2H, m) and 2.9 (2H, m) (CH$_2$CH$_2$ unit); 3.84 (3H, s, OMe); 6.84 (1H, dd, indole H6); 6.97 (1H, d, indole H2); 7.04 (1H, d, indole H4); 7.1–7.4 (6H, m, indole H7+Ph); and 8.00 (1H, br. s, indole NH).

EXAMPLE 13

1-(4-(N-(2-Hydroxy-3-(1-naphthyloxy)propyl)-N-methyl)amino)-2-phenylbutanoyl)-2,3,4,5,6,7-hexahydro-1H-azepine N-(2-Hydroxy-3-(1-naphthyloxy)propyl)-N-methylamine (9.43 mmol), 2,3,4,5,6,7-hexahydro-1H-[3-formyl-2-phenylpropanoyl]azepine (9.43 mmol), sodium triacetoxyborohydride (10.4 mmol) and acetic acid (10.4 mmol) in 1,2-dichloroethane (20 ml) is stirred overnight at room temperature and diluted with water (40 ml). The separated aqueous phase is washed with dichloromethane (2×30 ml) and the combined organic phases washed with brine (40 ml), water (40 ml), dried (Na2SO4) and concentrated to afford an oil. The crude product is chromatographed on alumina, gradient eluting with hexane:ethyl acetate (3:1 to 1:2), to give the title compound as an oil.

We claim:

1. A compound of formula

or a pharmaceutically acceptable salt thereof wherein each R is independently hydrogen or $C_{1-6}$ alkyl, $R^1$ and $R^2$ together with the nitrogen atom to which they are attached represent a hexahydroazepino ring which may be optionally substituted by one or more $C_{1-6}$ alkyl, aryl or aryl($C_{1-6}$)alkyl groups, $R^3$ is an aryl or heteroaryl radical, $R^4$ is hydrogen or $C_{1-6}$ alkyl, and $R^5$ is a group of formula

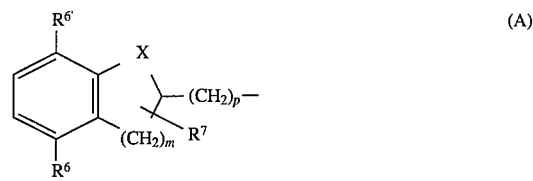

where X is —(CH$_2$)$_n$—, —OCH$_2$— or —SCH$_2$—, m is 0 or 1, n is 1, 2 or 3 and p is 0 or 1 such that (m+p) is 1 and that (m+n) is 1, 2 or 3, $R^6$ is hydrogen, $C_{1-6}$ alkyl, $C_{1-6}$ alkoxy, hydroxy, halogen, trifluoromethyl, ($C_{1-6}$) alkoxycarbonyl, carboxamido, nitro, cyano, amino, ($C_{1-6}$)alkylamino, di($C_{1-6}$)alkylamino or ($C_{1-6}$)alkylcarbonyl, $R^{6'}$ is hydrogen or halogen when X is —(CH$_2$)$_n$— and $R^{6'}$ is hydrogen when X is —OCH$_2$— or —SCH$_2$—, $R^7$ is hydrogen or lower alkyl or

where Y is —O—, —S— or —CH$_2$—,

Z represents a heteroaromatic ring fused on to the non-aromatic ring containing the Y group and $R^6$ is as defined above and one or more $R^6$ groups may be attached to the heteroaromatic ring and/or the non-aromatic ring or

where $R^8$ is a monocyclic or bicyclic heteroaryl group or

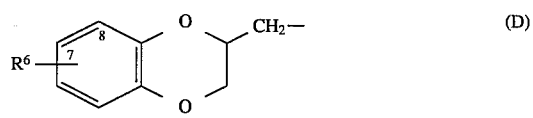

where $R^6$ is as defined above and the indicated 7, 8 positions may optionally be fused with a heteroaromatic ring or a further aromatic ring or or

where $R^9$ is a mono or bicyclic aryl or bicyclic heteroaryl group or $$R^9OCH_2CH_2— \tag{F}$$

where $R^9$ is as defined above.

2. A compound as claimed in claim 1 in which $R^5$ is a group of formula

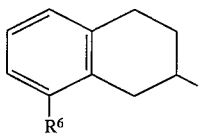

where $R^6$ is as defined in claim 1.

3. A compound as claimed in claim 1 in which $R^5$ is a group of formula

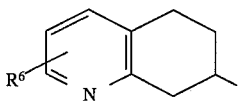

where $R^6$ is as defined in claim 1.

4. A compound as claimed in claim 1 in which $R^5$ is a group of formula

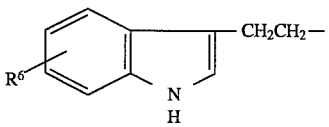

where $R^6$ is as defined in claim 1.

5. A compound as claimed in claim 1 in which $R^5$ is a group of formula

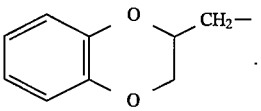

6. A compound as claimed in claim 1 in which $R^5$ is a group of formula

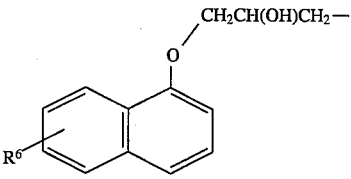

where $R^6$ is as defined above.

7. A compound as claimed in claim 1 in which $R^5$ is a group of formula

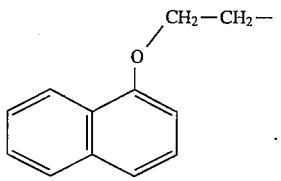

8. A pharmaceutical composition for use as a 5-$HT_{1A}$ antagonist comprising a therapeutically effective amount of a compound claimed in claim 1 in association with a pharmaceutically acceptable carrier.

9. A compound of claim 1 which is N-(2-(1,2,3,4-tetrahydro-8-methoxynaphthyl))-N-methyl-1-(4-amino-2-phenylbutanoyl)-2,3,4,5,6,7-hexahydro-1H-azepine or a pharmaceutically acceptable salt thereof.

10. A compound of claim 1 which is N-(7-(5,6,7,8-tetrahydroquinolinyl))-N-methyl-1-(4-amino-2-phenylbutanoyl)-2,3,4,5,6,7-hexahydro-1H-azepine or a pharmaceutically acceptable salt thereof.

11. A compound of claim 1 which is N-(2-(3-(5-methoxyindolyl))ethyl)-N-methyl-1-(4-amino-2-phenylbutanol)-2,3,4,5,6,7-hexahydro-1H-azepine or a pharmaceutically acceptable salt thereof.

12. A compound of claim 1 which is 1-(4-(2-(2,3-dihydro-1,4-benzodioxinyl)methylamino)-2-phenylbutanoyl)-2,3,4,5,6,7-hexahydro-1H-azepine or a pharmaceutically acceptable salt thereof.

13. A compound of claim 1 which is 1-(4-(1-(2-hydroxy-3-(1-naphthyloxy)propyl)amino)-2-phenylbutanoyl)-2,3,4,5,6,7-hexahydro-1H-azepine or a pharmaceutically acceptable salt thereof.

14. A compound of claim 1 which is 1-(4-(N-(2-(1-naphthyloxy)ethyl)-N-propylamino)-2-phenylbutanoyl)-2,3,4,5,6,7-hexahydro-1H-azepine or a pharmaceutically acceptable salt thereof.

15. A compound of claim 1 which is N-(2-(1,2,3,4-tetrahydro-8-methoxynaphthyl))-1-(4-amino-2-phenylbutanoyl)-2,3,4,5,6,7-hexahydro-1H-azepine or a pharmaceutically acceptable salt thereof.

16. A compound of claim 1 which is 1-(4-(N-(5-methoxy-3,4-dihydro-2H-1-benzopyran-3-yl)-N-methylamino)-2-phenylbutanoyl)-2,3,4,5,6,7-hexahydro-1H-azepine or a pharmaceutically acceptable salt thereof.

* * * * *